United States Patent [19]

Price, Jr.

[11] Patent Number: 4,750,904
[45] Date of Patent: Jun. 14, 1988

[54] POSTERIOR CHAMBER INTRAOCULAR LENS WITH IMPROVED FIXATION WHERE THE POSTERIOR CAPSULE IS NOT PRESENT TO SERVE AS A FIXATION PLATFORM

[76] Inventor: Francis W. Price, Jr., 5355 N. Kenwood Ave., Indianapolis, Ind. 46208

[21] Appl. No.: 846,705

[22] Filed: Mar. 31, 1986

[51] Int. Cl.⁴ ............................................. A61F 2/16
[52] U.S. Cl. ...................................................... 623/6
[58] Field of Search ........................................... 623/6

[56] References Cited

U.S. PATENT DOCUMENTS

| | | | |
|---|---|---|---|
| 3,922,728 | 12/1975 | Krasnov | 623/6 |
| 4,198,714 | 4/1980 | Jensen | 623/6 |
| 4,446,581 | 5/1984 | Blake | 623/6 |
| 4,485,499 | 12/1984 | Castleman | 623/6 |

OTHER PUBLICATIONS

"Lens Implantation' 30 years of Progress", by P. Leonard & J. Rommel, (Book), 1982, pp. 213-215.

Primary Examiner—Ronald L. Frinks
Attorney, Agent, or Firm—Woodard, Emhardt, Naughton, Moriarty & McNett

[57] ABSTRACT

A posterior chamber intraocular lens implant having improved fixation where there is no posterior capsule remaining to serve as a fixation platform. In addition to ciliary sulcus haptics, the lens implant has two oppositely disposed loops which serve as suture sites for the suturing of the implant directly to the iris. The loops, which are only so large so as to accommodate a 9-0 size suture thread, extend anteriorly from the optical lens to act as a cushion between the lens and the iris of the eye, and radially such that they align with the striae of the iris when the implant has been positioned within the eye, whereby inflamation of the iris is minimized.

10 Claims, 1 Drawing Sheet

POSTERIOR CHAMBER INTRAOCULAR LENS WITH IMPROVED FIXATION WHERE THE POSTERIOR CAPSULE IS NOT PRESENT TO SERVE AS A FIXATION PLATFORM

BACKGROUND OF THE INVENTION

1. Field of the Invention

The field of the invention is posterior chamber intraocular lenses. More particularly, the field of the invention is such lenses which are implanted either when or after an intracapsular procedure has been performed and where, therefore, the posterior capsule is no longer present to serve as a fixation platform.

2. Description of the Prior Art

There are generally two types of intraocular lens implants in use today—those implants which are positioned in front of the iris (anterior chamber lens implants) and those implants which are positioned behind the iris (posterior chamber lens implants). Anterior chambers lenses are simpler to implant than posterior chamber lenses, however, posterior chamber lenses present several advantages over anterior chamber lenses. One of those advantages concerns the preservation of the endothelial cells of the cornea.

The endothelium of the cornea is a one cell layer thick membrane which acts to pump fluids out of the cornea, thereby keeping the cornea clear. Endothelial cells of the cornea do not regenerate when they are destroyed, rather, adjacent endothelial cells expand to fill the area vacated by the destroyed cells. When the number of cells remaining reaches a critically low level, the patient may suffer from complications resulting from a lack of sufficient endothelial cells. Thus an operating surgeon ordinarily takes great care to avoid contact with endothelial cells during an intraocular implantation procedure, since if any cells are touched by a surgical instrument or suture material, they are destroyed and will not be replaced.

Because of its position in front of the iris, an anterior chamber lens implant is more likely to come in contact with endothelial cells of the cornea, in which case those cells will be destroyed. This is true not only during the implantation procedure, but while the implant is functionally in place as well. Furthermore, an hydrostatic charge on the surface of a plastic anterior chamber lens tends to pull endothelial cells away from the cornea.

Anterior chamber lenses possess another disadvantage verses posterior chamber lenses in that anterior chamber lenses can potentially block the filtration of fluids through the angle of the eye. This blocking of the natural filtration process of the eye creates an increased likelihood of glaucoma.

There are basically two general types of cataract removal techniques employed today—extracapsular and intracapsular procedures. In an extracapsular procedure, the capsule behind the lens (posterior capsule) is left intact, whereas in an intracapsular procedure, the posterior capsule is extracted in the course of the procedure.

After an extracapsular procedure, the posterior capsule can readily serve as a stable site for the lodging of a posterior chamber intraocular lens implant within the eye. Posterior chamber lenses generally take advantage of this fact by including haptics which extend from the lens portion of the implant into the ciliary sulcus of the eye where they maintain the lens in position and where there is no risk of the lens floating back into the eyeball.

With an intracapsular procedure, however, the capsule is no longer in place to retain a posterior chamber lens within the sulcus. The implant is therefore normally sutured into place by the surgeon. After an intracapsular procedure, lenses have been sutured into place by either tying the ciliary sulcus haptics to the iris or by using the positioning holes of the lens as suture sites. Also, various types of lenses have been specifically designed which have provided for some type of attachment to the iris. Examples of such lenses can be found in U.S. Pat. Nos. 3,866,249; 3,991,426; 4,110,848; 4,198,714; 4,304,012; 4,404,694; 4,316,291; and 4,336,582. Where posterior chamber lens implants have been so attached, however, they have tended to cause damage to the iris by rubbing against the iris tissue as the iris expands and contracts during focusing.

Thus prior to the present invention, where there has been no posterior capsule present to serve as a fixation platform for a posterior lens implant, the operating surgeon has either (1) implanted an anterior chamber lens, which tends to destroy irreplaceable endothelial cells of the cornea and increases the risk of glaucoma, or (2) attached a posterior chamber lens to the iris in one of the above ways which has tended to cause damage to the iris tissue.

SUMMARY OF THE INVENTION

The present invention generally relates to improved fixation for posterior chamber intraocular implants in procedures where there is no posterior capsule remaining to serve as a fixation platform. In one embodiment, suture sites are positioned about the perimeter of the optical lens portion of the implant. Each of the suture sites includes a small loop which is suitably sized to cooperatively accommodate a suture thread and which extends anteriorly from the optical lens to act as a cushion between the lens and the iris of the eye. The loops also extend radially such that they align with the striae of the iris when the implant has been positioned within the eye, whereby inflamation of the iris is avoided. A more complete understanding of the present invention, with its attendant advantages over the prior art, will be reached by a reading of the following specification and claims.

DESCRIPTION OF THE PREFERRED EMBODIMENT

Figure 1:
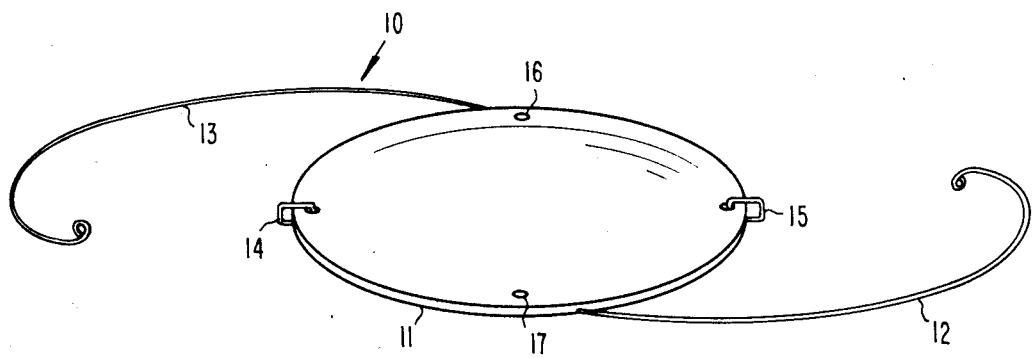
FIG. 1 is a perspective view of a posterior chamber intraocular lens implant according to the present invention.
Figure 2:
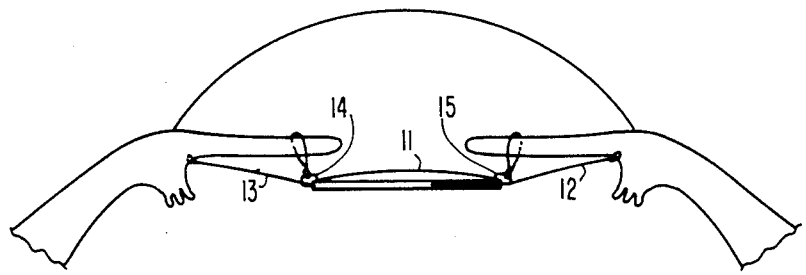
FIG. 2 is a side elevational view of the lens implant of FIG. 1 implanted within an eye.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now to the drawings (not drawn to scale), FIG. 1 shows a perspective view of an lens implant 10 according to the present invention. Lens implant 10 is a posterior chamber lens implant which is particularly designed for implantation either during or after an intracapsulary procedure where the posterior chamber capsule is no longer present to serve as a fixation platform. Lens implant 10 includes an optical lens portion 11 and attachment means for attaching the optical lens portion 11 within the posterior chamber of the eye. The attachment means can include ciliary sulcus haptics 12 and 13, and small iris suture receiving loops 14 and 15. These loops provide two suture sites about the perimeter of optical lens 11 and are equidistantly and oppositely disposed with respect to each other. The small loops 14 and 15 are suitably sized to cooperatively accommodate a suture thread and for implantation on the posterior side of the iris. On lens portion 11, there are two positioning holes 16 and 17.

Haptics 12 and 13 hold implant 10 in place by seating in the ciliary sulcus 22 and may have any of a wide variety of configurations. In an extracapsulary procedure, this lodging is sufficient to stably fix implant 10 in position. However, where the posterior capsule is no longer present, haptics 12 and 13 alone can not reliably serve this function. Iris suture loops 14 and 15 provide the additional fixation that is needed where the posterior capsule is not present. Iris suture loops 14 and 15 also serve a cushioning functioning between the iris 21 and lens 11. Loop 14 and 15 ride on the back or posterior surface of the iris but lens 11, itself, does not. Because there is less contact with the iris, there is less inflammation and less pigment is liberated.

Figure 3:
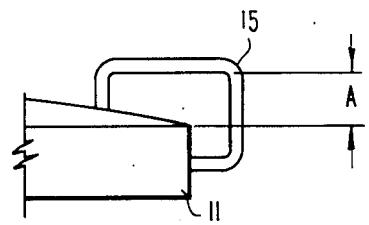
FIG. 3 is a fragmentary cross-sectional view of a portion of the lens implant of FIG. 1.

FIG. 3 is a close up view showing the attachment of loop 15 to lens portion 11. Space A between loop 15 and lens portion 11 should be large enough to accommodate a suture thread but no larger. The anterior extension of loop 15 from lens portion 11 provides cushioning between lens portion 11 and iris 21 during implantations. However too large of an anterior space A will lead to instability. Sizing loop 15 to cooperatively accommodate a 9-0 suture will serve to provide the cushioning effect desired and yet be not so large so as to cause instability. Loops 14 and 15 may either be formed by a filament material such as polypropylene or polymethylmethacrylate attached to lens portion 11 or may be part of an integrally molded design.

It should further be observed that loop 15 is oriented in a radial fashion with respect to lens 11. This radial orientation serves to align loops 14 and 15 with the striae of the iris. Because loops 14 and 15 are so alligned with the striae of the iris, scarring or chapping of the iris is reduced to a minimum. Such scarring and chapping of the iris is to be avoided, since it can liberate pigment from the back surface of the iris and can cause a chronic inflammation of the iris. Furthermore, the chronic discharge of pigment that can clog the trabecular meshwork in the angle of the anterior chamber where the fluid filters out of the eye. Such blockage can lead to increased pressure in the eye and, eventually, glaucoma.

It is to be further noted that loops 14 and 15 may also serve the function of positioning holes 16 and 17 in the placement of lens 10 within the eye. Therefore positioning holes 16 and 17 are no longer required with the present invention.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A posterior chamber intraocular lens implant comprising: an optical lens; and attachment means for attaching said optical lens to the eye within the posterior chamber of the eye, said attachment means including two suture sites, said suture sites being positioned about the perimeter of said optical lens and being oppositely disposed with respect to each other on said optical lens, each of said suture sites including a small loop suitably sized to cooperatively accommodate a suture thread and for implantation on the posterior side of the iris, each of said loops extending anteriorly from said optical lens.

2. The posterior chamber intraocular lens implant of claim 1 in which said loops extend radially from said optical lens, wherein said loops align with the striae of the iris of the eye when said implant is implanted within the eye of a patient.

3. The posterior chamber intraocular lens implant of claim 1 in which said loops are constructed of polypropylene filament material.

4. The posterior chamber intraocular lens implant of claim 1 in which said loops are constructed of polymethylmethacrylate.

5. The posterior chamber intraocular lens implant of claim 1 in which said loops are sized to cooperatively accommodate a size 9-0 suture thread.

6. A posterior chamber intraocular lens implant comprising: an optical lens; attachment means for attaching said optical lens to the eye within the posterior chamber of the eye, and cushioning means for cushioning said implant against the posterior surface of the iris of the eye when said implant is implanted within the eye of a patient, said cushioning means including a plurality of loops, said loops being equidistantly disposed about the perimeter of said optical lens and extending anteriorly and radially from said optical lens.

7. The posterior chamber intraocular lens implant of claim 6 in which said loops are suitably sized to cooperatively accept a suture thread for attachment to the iris of the eye when said implant is implanted within the eye of a patient.

8. The posterior chamber intraocular lens implant of claim 6 in which said loops are constructed of polypropylene material.

9. The posterior chamber intraocular lens implant of claim 1 in which said loops are constructed of polymethylmethacrylate.

10. The posterior chamber intraocular lens implant of claim 7 in which said loops are sized to cooperatively accommodate a size 9-0 suture thread.

* * * * *